(12) United States Patent
Berman

(10) Patent No.: US 6,384,081 B2
(45) Date of Patent: May 7, 2002

(54) TREATMENT OF DISEASES OF THE EYE CHARACTERIZED BY THE FORMATION OF METALLOPROTEINASE

(76) Inventor: Charles L. Berman, 211 Central Park West, New York, NY (US) 10024

( * ) Notice: Subject to any disclaimer, the term of this patent is extended or adjusted under 35 U.S.C. 154(b) by 0 days.

(21) Appl. No.: 09/169,660

(22) Filed: Oct. 9, 1998

(51) Int. Cl.⁷ .............................................. A61K 31/165
(52) U.S. Cl. ....................................... 514/621; 514/912
(58) Field of Search ................................ 514/169, 192, 514/912, 199, 621

(56) References Cited

U.S. PATENT DOCUMENTS 5,260,059 A * 11/1993 Acott et al. ............... 424/94.67
5,308,839 A * 5/1994 Golub et al. ................. 514/152

* cited by examiner

*Primary Examiner*—Zohreh Fay
(74) *Attorney, Agent, or Firm*—Stephen E. Feldman, P.C.

(57) ABSTRACT

The instant invention provides a method of inhibiting the formation of metalloproteinase and its species, within the eyes of a patient inflicted with at least one form of retinitis characterized by the presence of metalloproteinase, through the administration of an effective dosage that includes an a tetracycline analog, its salts, conjugates or derivatives. In an alternate preferred embodiment of the invention, the dosage includes at least one other therapeutic substance in effective combination with a tetracyline analog.

7 Claims, No Drawings

TREATMENT OF DISEASES OF THE EYE CHARACTERIZED BY THE FORMATION OF METALLOPROTEINASE

BACKGROUND OF THE INVENTION

The instant invention broadly relates to inhibition of the formation of substances which promote the advancement of diseases that can cause blindness, More specifically, the invention inhibits the formation of species of metalloproteinase which are formed as a product of diseases of the eye. Still more specifically, in a preferred embodiment, the invention provides for the administration of an effective amount of a tetracycline analog, its salts, conjugates or derivatives for inhibiting the formation of metalloproteinase species including collagenase, elastase, and most particularly, geletanase in various parts of the eye, more particularly, the retina and/or vitreous of a patient inflicted with an advancing eye disease, most particularly, at least one of any form of retinitis characterized by the formation of metalloproteinase and its species. In an alternate preferred embodiment, the invention provides for the administration of an effective amount of a tetracycline analog, its salts, conjugates or derivatives, in synergistic combination with at least one other therapeutic substance, its salts, conjugates or derivatives, for inhibiting the formation of metalloproteinase species including collagenase, elastase, and most particularly, geletanase in various parts of the eye, more particularly, the retina and/or vitreous of a patient inflicted with an advancing eye disease, most particularly, at least one of any form of retinitis characterized by the formation of metalloproteinase and its species.

Mammalian extracellular matrix (ECM) turnover is thought to be initiated by the secretion of several proteinases, which cause partial degradation of specific matrix components. Thereafter, the disrupted matrix components are taken up and degraded further within lysosomal vesicles. Interstitial collagenase, gelatinase or type IV collagenase, and stromelysin or proteoglycanase are members of a family of matrix metalloproteinases with sufficient diversity in substrate specificities to achieve this initial disruption. These metalloproteinases are active at neutral pH and are known to be secreted by a variety of different cell types.

Interstitial collagenase (MMP-1), also called type I-II-III collagenase is an endopeptidase capable of cleaving each of the α-chains of the collagen triple helix at a Gly-Ile or Gly-Leu site located about one-fourth the distance from the carboxy-terminus. This produces thermally unstable soluble fragments about one-fourth and three-fourths the original size, which in turn are susceptible to degradation by gelatinases. Hasty et al., J. Biol. Chem. 262, 10048–10052 (1987) report by immunologically distinct interstitial collagenases from fibroblasts and neutrophils. The latter has a higher catalytic rate toward Type I collagen, while the former is more active toward Type III collagen. Goldberg et al., J. Biol. Chem. 261, 6600–6605 (1986) report that there are two forms of interstitial collagenase produced by human skin fibroblasts-one, an unmodified procollagenase, Mr≈52 kDa, and the other, a glycosidated form, Mr≈57 kDa. None of these interstitial collagenases appear capable of degrading Type IV or V collagen.

Ocular tissues have been shown to secrete interstitial collagenase, and the secretion has been shown to be controlled by various extracellular factors. Johnson-Wint Proc. Natl. Acad. Sci. USA 77, 5331–5335 (1980) demonstrated that cornea stromal cell collagenase production is regulated by simulators and inhibitors secreted by corneal epithelial cells. In an earlier report Johnson-Muller et al., Pro. Natl. Acad. Sci. USA 75, 4417–4421 (1978) described other soluble chemical and biological agents capable of stimulating macrophages to secrete collagenase. These include: neutral proteases, prostaglandins, bacterial endotoxins, colchicine, phorbol myristic acid, and cytochalasin B. Others (Beaman et al., Exp. Eye Res. 22, 209–218 (1976)) have described regulation of collagenase activity in corneal tissue by cyclic-AMP.

Gelatinase(MMP-2) or Type IV collagenase is a neutral metalloproteinase capable of hydrolyzing basement membrane type IV collagen into the characteristic ¼ amino-terminal ¾ carboxyl-terminal fragments. The protein is secreted by a variety of cells, for example fibroblasts and tumor cells, as a 70 kDa Type IV procollagenase. This latent proenzyme is converted to a 62 kDa Type IV collagenolytically active enzyme by the autocatylitic removal of an 80 residue peptide fragment from the amino terminus (Stetler-Stevenson et al., J. Biol. Chem. 264, 1353–1356 (1989). In addition to Type IV collagenolytic activity, gelatinase has been reported to have activity toward gelatin (degraded Type I, II and III collagen), Type V and Type VII collagen, fibronectin, and Lenin. (See for example Murphy et al., J. Biol. Chem. 199, 807–811 (1981)). This enzyme is known to be inhibited by EDTA and 1,10-phenanthroline, and to require Zn and/or Ca for its activity. Hibbs et al., J. Biol. Chem. 260, 2493–2500 (1985) has demonstrated the enzyme to be rapidly secreted from neutrophils stimulated with phorbol myristate acetate (TPA).

Stromelysin (MMP-3) is a neutral metalloendopeptidase secreted by various cell types. This enzyme has been reported to have a 55% homology with interstitial collagenase. Chin et al., J. Biol. Chem. 260, 12367–12376 (1985) demonstrated that rabbit synovial fibroblasts induced by agents such as TPA, Cytochalasin B, and poly-(2-hydroxyethyl methacrylate) secrete prostromelysin, Mr=51 kDa. This metal (Zn, Ca) dependent proteinase was activated by trypsin and 4-aminophenolmercuric acetate (AMPA) to a Mr≈41 kDa form with activity toward casein, cartilage proteoglycans, α-(1)-proteinase inhibitor, immunoglobulin G2a, fibronectin, laminin, and Type IV collagen. In addition to be inhibited by metal chelators such as EDTA and 1,10-phenanthroline, the enzyme is normally secreted from endothelial cells complexed with tissue inhibitor of metalloproteinases (TIMP), Herron et al., J. Biol. Chem. 261, 2810–2813 (1986). The complete sequence of human skin fibroblast stromelysin has been determined by Wilhelm, et al., Proc. Natl. Acad. Sci. USA 84, 6725–6729 (1987). These authors demonstrated great homology between human stromelysin and rat transin, an oncogene transformation-induced protein. The induction of transin transcription by various oncogenes and epidermal growth factor (EGF) was described by Matrisian et al., Mol. Cell. Biol. 6, (1986). Other transforming factors shown to induce stromelysin in human fibroblasts include tumorgenic agents such as u.v. light, mitomycin-c, and interleukin-1 (IL-1). Whitham, et al., J. Biol. Chem. 240, 913–916 (1986).

The members of the foregoing family of matrix metalloproteinases share many structural and functional similarities, including inhibition by an endogenous inhibitor, tissue inhibitor of metalloproteinases (TIMP). TIMP from human amniotic fluid and cultured fetal lung fibroblasts has been sequenced, and was reported to be immunologically identical to a variety of forms of the protein found in other tissues or body fluids, these inhibitors range in size from Mr≈20–28 kDa. It appears that a variety of cells coordinate synthesis of MMP-1, MMP-2 and MMA-3 with their specific inhibitor TIMP in vivo (Herron et al., J. Biol. Chem. 261, 2814–2818 (1986)).

A variety of agents arc known to stimulate secretion of both MMPs and TIMP from various cells; however, few are known to do so differentially. One exception, reported by Duncan et al., Biochemical Pharmacology 32, 3853–3858 (1983) is Razoxane, which inhibited collagenase production and stimulated TIMP production.

The existence of these metalloproteinases and their inhibitor in ocular tissue, other than cornea and sclera, has not been demonstrated. Furthermore, the relationship of these secreted proteins to ocular disease, especially glaucoma and retinal disease, has not been ascertained.

Broadly, the instant invention is applicable to any eye disease characterized by the presence of metalloproteinase and its species collagenase, elastase and geletinase. The invention is more particularly applicable to any form of retinitis characterized by the presence of metalloproteinase and its species collagenase, elastase and geletinase. The tern "retinitis" refers generally to an inflammation of the retina. The term embraced numerous species. Included among, but not necessarily limited to these species are: actinic retinitis—a species caused by exposure to actinic light rays; retinitis albuminuria—species associated with kidney disease; apoplectic retinitis-a species characterized by extravasation of blood within the retina; central angiospastic retinitis or centralis serosa—also known as central serious retinopathy; Coat's retinitis—exudative retinopathy; diabetic retinitis—retinitis occurring in diabetes; retinitis disciformans—a degenerative disease of the retina marked by an elevated grayish white mass in the macular region of both eyes (also called central disk shaped retinopathy); exudate retinitis—exudative retinopathy; retinitis gravitdarum—a garvidic inflammation of the retina occurring along with the albuminuria of pregnancy; hemorrhage retinitis—retinitis marked by profuse retinal hemorrhage; hypertensive retinitis—retinitis occurring in the course of arterial hypertension; Jacobson's retinitis—syphilitic retinitis; Jensen's retinitis-retinochoroiditis juxtapillaris; leukemic retinitis—a variety seen in leukemia, and marked by hemorrhage and paleness of the retina by the location of septic emboli in the retinal vessels; retinitis nephritica—retinal changes associated with nephritis, also call renal retinitis; retinitis pigmentosa—a group of diseases, frequently hereditary, and marked by progressive loss of retinal response (as elicited by the electroretinogram), retinal atrophy, a attenuation of the retinal vessels, and clumping of the pigment, with contraction of the field of vision. It may be transmitted as a dominant, recessive, or X-linked trait and is sometimes associated with other genetic defects; retinitis proliferans or proliferating retinitis—a condition sometimes resulting from intraocular hemorrhage, with the formation of fibrous tissue bands extending into the vitreous from the surface of the retina. Retinal detachment is sometimes a sequel; retinitis puntata albescens—a variety characterized by the presence of minute white spots in the fundus; retinitis puntata retinitis—a form marked by the presence of a number of white or yellowish spots scattered over the fundus; punctate retinitis—a form marked by the presence of white or yellowish spots scattered over the fundus; renal retinitis—also know as nepritica; serous retinitis—a simple inflammation of the superficial layers of the retina; solar retinitis—a species of retinitis due to excessive exposure to sunlight; splenic retinitis—also known as leukemic retinitis, retinitis stellata, a star-shaped figure in the macular area of the retina seen in various conditions; striate retinitis, a for marked by the presence of gray or yellowish streaks just back of the retinal vessels; suppurative retinitis—retinitis due to pyemic infection; syplilitic retinitis or retinitis syphilitica—retinitis complicating syphilitic iritis; uremic retinitis—retinitis occurring in uremia; retinal microvasculopathy—commonly known as AIDS retinopathy, is seen in 100% of AIDS patients. It is characterized by intra retinal hemorrhages, micro aneurysms, Roth spots, cotton-wool spots (micro infarctions of the nerve fiber layer) and perivascular sheathing; cytomegalovirus retinitis—now one of the most common AIDS related opportunistic infections. It usually causes a transient, influenza-like illness followed by lifelong immunity; Herpes simplex retinitis—(also referred to as acute retinal necrosis or ARN) has been described in both immunocompetent and AIDS patients. In AIDS patients, it causes a fulminant, necrosing retinitis with significant intraocular inflammation; Herpes zoster retinitis—(also called progressive outer retinitis or PORN) usually follows reactivation of cutaneous zoster or shingles. The retinitis is multi focal, usually bilateral, and rapidly progressive. There is very little intraocular inflammation, distinguishing this from Herpes simplex retinitis; Toxoplasma retinochoroiditis—also seen in both immunocompetent and AIDS patients. In AIDS patients there is a greater tendency for multi focal disease and large areas of retinal necrosis. There is usually concurrent CNS toxoplasmosis with the classic ring enhancing lesion seen on MRI.

Commonly, these variously species are often complicated by the formation of metalloproteinace, and its species, collagenase, elastase and, and in particular, geletinase.

Various United States Patents have recognized the presence of metalloproteinase as a product of diseases of the retina. Exemplary of these patents, U.S. Pat. No. 5,260,059 relates to a method of treating ocular disease by modulating cellular secretion of a family of matrix metalloproteinase and their inhibitor. Specifically, differential stimulation of secretion of interstitial collagenase, gelatinase or type IV collagenase, stromelysin or proteoglycanase, and their tissue glycoprotein inhibitor is employed to treat open-angle glaucoma, retinal degeneration and detachment, ocular neovascularization and diabetic retinopathy.

U.S. Pat. No. 5,716,981 discloses that the pathology of diabetic retinopathy is thought to be similar to that of neovascular glaucoma. In particular, background diabetic retinopathy is believed to convert to proliferative diabetic retinopathy under the influence of retinal hypoxia. Generally, neovascular tissue sprouts from the optic nerve (usually within 10 mm of the edge), and from the surface of the retina in regions where tissue perfusion is poor. Initially the capillaries grow between the inner limiting membrane of the retina and the posterior surface of the vitreous. Eventually, the vessels grow into the vitreous and through the inner limiting membrane. As the vitreous contracts traction is applied to the vessels, often resulting in shearing of the vessels and blinding of the vitreous due to hemorrhage. Fibrous traction from scaring in the retina may also produce retinal detachment. The conventional therapy of choice is panretinal photocoagulation to decrease retinal tissue, and thereby decrease retinal oxygen demands. Although initially effective, there is a high relapse rate with new lesions forming in other parts of the retina. Complications of this therapy include a decrease in peripheral vision of up to 50% of patients, mechanical abrasions of the cornea, laser-induced cataract formation, acute glaucoma, and stimulation of subretinal neovascular growth (which can result in loss of vision). As a result, this procedure is performed only when several risk factors are present, and the risk-benefit ratio is clearly in favor of intervention. Proliferative diabetic retinopathy may be treated by injection of an anti-angiogenic factor(s) (or anti-angiogenic composition) into the aqueous humor or the vitreous, in order to increase the local concentration of anti-angiogenic factor in the retina. This treatment should be initiated prior to the acquisition of severe disease requiring photocoagulation. Within other embodiments of the invention, arteries which feed the neovascular lesions may be embolized (utilizing anti-angiogenic compositions)

Other United States Patents recognizing the link between retinal diseases and metalloproteinase are: U.S. Pat. No. 5,770,580; U.S. Pat. No. 5,744,442; U.S. Pat. No. 5,693,629; U.S. Pat. No. 5,679,339; U.S. Pat. No. 5,681,706; and, U.S. Pat. No. 5,695,761.

Therapeutic eye treatment with various drugs is old in the prior art. U.S. Pat. No. 4,186,184 to Sabatine, et al, for instance, teaches a method for administering drug to a preselected surface of the lid of an eye which comprises the steps of: (a) placing in the eye a therapeutic system comprising: a drug, a drug delivery module sized, shaped and adapted as a platform for comfortable retention in the eye and for housing the drug, said module including a delivery portal defining a surface area of the module for releasing the drug from the system; and,(b) positioning the system in the eye by orienting the portal towards the preselected internal surface of the lid for effective administration of drug thereto. Further, the Patent cites: J. Shell & R. Baker, Diffusional Systems for Controlled Release of Drugs lo the Eye, Ann. Ophthalmol. 6:1037 (1974); J. Shell, Ocular Therapy by Controlled Drug Delivery: the Ocusert System, Ophthalmic Surg, 5.73 (1974); H. Armaly and K. Rao, The Effect of Pilocarpine Ocusert with Different Release Rates on Ocular Pressure, Invest. Ophthalmol. 12, 491 (1973); V. A. Place, M. Fisher, S. Herbst, L. Gordon & R. C. Merrill, Comparative Pharmacologic Effects of Pilocarpine Administered to Normal Subjects by Eyedrops or by Ocular Therapeutic Systems, Amer. J. Ophthalmol. 80, 706 (1975); S. K. Chandrasekaran, Harriet Benson & John Urquhart, Alza Corp., Palo Alto, Calif., Chapter 7, "Methods to Achieve Controlled Drug Delivery-The Biomedical Engineering Approach", pp. 557–572, 590–591; Robinson, J. R. Ed., "Sustained & Controlled Release Drug Delivery Systems, Marcel Dekker, Inc. New York, N.Y. (1978).

U.S. Pat. No. 5,532,227 to Golub, et al teaches a method for treating mammals suffering from excessive extracellular protein glycosylation which is associated with diabetes, scleroderma and progeria by administering to the mammal a tetracycline which effectively inhibits excessive protein glycosylation.

Inhibition of metalloproteinase activity with various species of non-antimicrobial tetracycline, is well known in the prior art. For instance, U.S. Pat. No. 5,321,017 to Golub, et al teaches a method for treating mammals suffering from rheumatoid arthritis and other tissue-destructive (chronic inflammatory or other) conditions associated with excess metalloproteinase activity which comprises: administering to the mammal an amount of a tetracycline that is effectively anti-metalloproteinase, but that is not effectively antimicrobial, and an amount of non-steroidal anti-inflammatory agent which, when combined with the effectively anti-metalloproteinase amount of tetracycline, results in a significant reduction of tissue destruction and/or bone loss.

U.S. Pat. No. 5,045,538 to Schneider, et al teaches a method for treating mammals suffering from skeletal muscle wasting and/or intracellular protein degradation of skeletal muscle systems by administering to the mammal an amount of tetracycline which results in a significant reduction of the muscle wasting and protein degradation. In addition, there is also disclosed a method of increasing the protein content of skeletal muscle systems of mammals by administration of tetracyclines. The tetracyclines useful in the above methods are both antimicrobial and non-antimicrobial. In a preferred embodiment, the method of treatment utilizes a non-antimicrobial tetracycline such as dedimethylaminotetracycline U.S. Pat. No. 5,324,634 to Zucker teaches diagnostic agents and methods for detecting the presence of metastatic activity in biological samples such as plasma. The agent and method preferably immunologically detect matrix metalloproteinases in complexed form with endogenous inhibitors of MMP's. A kit for detecting the metalloproteinases is also disclosed.

U.S. Pat. No. 5,260,059 to Acott, et al relates to a method of treating ocular disease by modulating cellular secretion of a family of matrix metalloproteinases and their inhibitor. Specifically, differential stimulation of secretion of interstitial collagenase, gelatinase or type IV collagenase, stromelysin or proteoglycanase, and their tissue glycoprotein inhibitor is employed to treat open-angle glaucoma, retinal degeneration and detachment, ocular neovascularization and diabetic retinitis.

U.S. Pat. No. 5,595,885 to Stetler-Stevenson, et al teaches an isolated protein of 21,600 Da which binds to both latent and activated te IV collagenase with high affinity at 1:1 molar stoichiometry, thereby abolishing enzyme activity. The protein is purified by affinity chromatography on solid phase metalloproteinase, or solid phase metalloproteinase substrates which bind the enzyme-inhibitor complex. The complete primary structure of this protein (initially called CSC-21K), as determined by sequencing overlapping peptides spanning the entire protein, reveals homology with a protein called TIMP, Tissue Inhibitor of Metalloproteinases. In addition, a cDNA for this novel inhibitor; now designated TOP-2, was cloned from a melanoma cell and its sequence was compared with that of human TIMP-1. Northern blots of melanoma cell mRNA showed two distinct transcripts of 0.9 b and 3.5 kb which are down-regulated by transforming growth factor-$\beta$, and are unchanged by phorbol ester treatment. The inhibitor of the present invention may be used for treatment of pathologic conditions resulting form inappropriate degradation of extracellular matrix molecules by matrix metalloproteinases, such as metastatic neoplasia, myocardial infarction, and arthritis. Therapeutic treatments using this inhibitor may include formulations for inhalation and inclusion complexes adapted for buccal or sublingual administration, or administration of a recombinant DNA molecule which expresses a DNA segment that encodes the matrix metalloproteinase inhibitor of this invention.

U.S. Pat. No. 5,308,839 to Golub, et al teaches a method for treating mammals suffering from rheumatoid arthritis, other tissue-destructive conditions, and chronic inflammatory or other conditions associated with excess metalloproteinase activity which comprises: administering to the mammal an amount of a tetracycline that is effectively anti-metalloproteinase, but that is not effectively antimicrobial, and an amount of a non-steroidal anti-inflammatory agent which, when combined with the effectively anti-metalloproteinase amount of tetracycline, results in a significant reduction of tissue destruction and/or bone loss.

U.S. Pat. No. 5,532,227 to Golub, et al teaches a method for treating mammals suffering from excessive extracellular protein glycosylation which is associated with diabetes, scleroderma and progeria by administering to the mammal a tetracycline which effectively inhibits excessive protein glycosylation.

U.S. Pat. No. 5,308,839 to Golub, et al teaches a method for treating mammals suffering form rheumatoid arthritis, other tissue-destructive conditions, and chronic inflammatory or other conditions associated with excess metalloproteinase activity comprising administering to the mammal an amount of a tetracycline that is effectively anti-metalloproteinase, but that is not effectively antimicrobial, and an amount of a non-steroidal anti-inflammatory agent which, when combined with the effectively anti-metalloproteinase amount of tetracycline, results in a significant reduction of tissue destruction and/or bone loss.

U.S. Pat. No. 5,223,248 to McNamara, et al teaches a method of inhibiting plaque formation on mammalian tooth surfaces. THE method includes contacting the tooth surfaces with an effective amount of a non-antibacterial tetracycline. In a preferred embodiment, such tetracyclines are included in various oral hygiene products such as dentifrices, lozenges, chewing gums and the like to contact the tooth surfaces and prevent plaque accumulation thereon.

U.S. Pat. No. 5,045,538 to Schneider, et al teaches a method for treating mammals suffering from skeletal muscle wasting and/or intracellular protein degradation of skeletal muscle systems by administering to the mammal an amount of tetracycline which results in a significant reduction of the muscle wasting and protein degradation. In addition, there is also disclosed a method of increasing the protein content of skeletal muscle systems of mammals by administration of tetracyclines. The tetracyclines useful in the above methods are both antimicrobial and non-antimicrobial. In a preferred embodiment, the method of treatment utilizes a non-antimicrobial tetracycline such as dedimethylaminotetracycline (CMT).

In a journal article entitled "ALBRECHT VON GRAEFES ARCHIV FUR KLINISCHE UND EXPERIMENTELLE OPHTHALMOLOGIE," dated November 1977, a drug treatment for laboratory induced blindness in rabbits was proposed. By using radioactive tracer method the distribution of intravenously injected doxycycline of 7 mg/kg was studied in the rabbit eye. Long-lasting antibiotic concentration of 1 microgram/g or more was measured from all vascularized ocular structures. Vitreous body doxycycline concentration, almost equal to that of aqueous humor, was 0.3 microgram/g. Doxycycline concentration in the cornea exceeded that in the aqueous humor. In all vascularized ocular structures plasma antibiotic concentration was at least once achieved, indicating good penetrability of doxycycline into the tissues. This good penetrability is obviously related to the high lipoidsolubility of doxycycline, whereas its high protein binding is reflected in low concentrations in the aqueous humor.

In a second journal article which appeared in a journal named: "BULLETIN DE LA SOCIETE BELGE D OPHITALMOLOGIE," ISSN:0081-0746, published in 1989, another experiment involving laboratory blinded rabbits was described. In the experimental study of the intraocular penetration of six drugs with therapeutic effect on toxoplasma, a direct and an indirect method were used. The penetration of six drugs administered sub-conjunctival, ret-robulbar and intramuscular in one shot is measured in the anterior chamber, the vitreous and the retina-choroid of a health rabbit eye. The best results are obtained for: spiramycin, trimethoprim-sulfamethoxazole and clindamycin. The therapeutic efficiency of four drugs on infected rabbit eyes with toxoplasma are studied using an indirect method: pyrimethamine and especially doxycycline have a positive elect.

In a second journal article which appeared in a journal named: "INVESTIGATIVE OPHTHALMOLOGY AND VISUAL SCIENCE," ISSN:0146-0404, dated July 1989, the inhibitory potency of four classes of compounds that inhibit corneal ulceration (thiols, tetracyclines, sodium citrate and sodium ascorbate) was assessed with collagenase purified from culture medium of alkali-burned rabbit corneas. The most potent inhibitor, a beta-mercaptomethyl tripeptide HSCH2(DL)CH[CH2 CH(CH3)2]CO-Phe-Ala-NH2, exhibited 50% inhibition (IC50) at approximately 10 nM using the synthetic metalloproteinase substrate Dnp-Pro-Leu-Gly-Leu-Trp-Ala-D-Arg-NH2. The inhibitor was somewhat less potent with type 1 collagen as substrate (IC50 between 1 and 3 microM), possibly because autooxidation of the essential—SH moiety of the inhibitor occurred during the longer time required for assay with the natural substrate. An N-carboxylalkyl tripeptide, CH3(CH2)2(DL)CH-(COOH)-Leu-Phe-Ala-NH2, was less potent (IC50=25 microM) than the thiol peptide. N-acetylcysteine, which is used to treat corneal ulceration, gave IC50 values of 2.7 mM and less than 10 mM with the synthetic and natural substrates, respectively. The IC50 values for the tetracyclines using the synthetic substrate were 15, 190 and 350 microM for doxycycline, minocycline and tetracycline, respectively. Inhibition by sodium citrate, but not the tetracyclines, could be reversed by excess Ca2+. Sodium ascorbate did not inhibit collagenase-mediated hydrolysis of either collagen or the synthetic substrate, thus indicating that the mechanism by which this agent inhibits corneal ulceration is not related to inhibition of collagen degradation by collagenase.

In another article; ISSN:0277-3740, dated September 1993, Journal entitled "CORNEA," the effects of doxycycline hyclate on epithelial healing in vivo in the rabbit alkali-burn model was examined. Twelve 2–3-kg Dutch belted rabbits were divided into three groups and received standard bilateral alkali burns (1 N sodium hydroxide for 30 s in an 11-mm circular plastic well). In group 1, two rabbits (four eyes) served as untreated controls. In group 2, five rabbits (10 eyes) received doxycycline hyclate (1.5 mg/kg) orally daily for 14 days. In group 3, five rabbits (10 eyes) received doxycycline hyclate (5 mg/kg) orally daily for 14 days. The epithelial defects were drawn and photographed on alternate days, after fluorescein staining. At conclusion, extracts of the corneas were evaluated for collagenase activity. At 14 days, the mean percentage of epithelial defects results in groups 1–3 were 50.0, 50.7, and 7.1%, respectively. Using the Wilcoxon rank sum test (two tailed), the differences were found to be statistically significant (p=0.0015). Preliminary data indicated that oral doxycycline, administration also decreased the collagenase activity in corneas obtained form these animals. Our preliminary findings indicated that systematically administered doxycycline hyclate, 5 mg/kg/day, promotes corneal reepithelialization in the rabbit alkali-burn model, a result, perhaps, of the drug's ability to inhibit excessive collagenase activity.

The foregoing United States patents and technical articles are incorporated in their entireties and have been cited here in great part for enabling the person of ordinary skill to practice the instant invention.

To date, there exists no effective drug protocol for the treatment of substantially all forms of retinitis characterized by the presence of metalloproteinase and its species, in human patients. It would be of great advantage to the art of eye medicine to provide such a protocol.

SUMMARY OF THE INVENTION

The instant invention in large part solves the problems of the prior and fulfills a long felt need by providing a treatment for a patient inflicted with an eye disease characterized by the presence of metalloproteinase and its species.

The instant invention provides a method of treating an eye disease characterized by the presence of metalloproteinase and its species, with an effective dosage of a drug or combination of drugs sufficient to provide an antimicrobial level of concentration of the drug in the body of the patient.

The instant invention provides a method of treating an eye disease characterized by the presence of metalloproteinase and its species, with an elective dosage of a drug or combination of drugs sufficient to provide a non-antimicrobal level of concentration of the drug in the body of the patient.

The instant invention provides a method of treating a patient who is inflicted with at least one form of retinitis, characterized by the presence of metalloproteinase and its species, with an effective dosage of a tetracycline analog, its salts, conjugates or derivatives, alone or in combination with at least one other therapeutic substance, sufficient to provide a non-antimicrobal level of concentration of the analog, its salts, conjugates or derivatives, alone or in combination with at least one other therapeutic substance, in the body of the patient.

The instant invention provides a method of treating a patient who is inflicted with at least one form of retinitis characterized by the presence of metalloproteinase and its species, with an effective dosage of a tetracycline analog, its salts, conjugates or derivatives, alone or in combination with at least one other therapeutic substance, sufficient to provide an antimicrobal level of concentration of the analog, its salts, conjugates or derivatives, alone or in combination with at least one other therapeutic substance, in the body of the patient.

The instant invention provides a method of treating a patient who is inflicted with at least one form of retinitis characterized by the presence of metalloproteinase and its species, with an effective dosage of a tetracycline analog, its salts, conjugates or derivatives, alone or in combination with at least one other therapeutic substance, sufficient to provide it non-antimicrobal level of concentration of the analog, its salts, conjugates or derivatives, alone or in combination with at least one other therapeutic substance, in the retina and/or vitreous of the eyes of the patient.

The instant invention provides a method of treating a patient who is inflicted with at least one form of retinitis, characterized by the presence of metalloproteinase and its species, with an effective dosage of a tetracycline analog, its salts, conjugates or derivatives, alone or in combination with at least one other therapeutic substance, sufficient to provide a antimicrobal level of concentration of the analog, its salts, conjugates or derivatives, alone or in combination with at least one other therapeutic substance, in the retina and/or vitreous of the eyes of the patient.

The instant invention provides a method of treating a patient who is inflicted with at least one form of retinitis, characterized by the presence of metalloproteinase and its species, with an effective dosage of a tetracycline analog, its salts, conjugates or derivatives sufficient to inhibit the formation of gelatinase in the vitreous of the eyes of the patient.

The instant invention provides a method of treating a patient who is inflicted with at least one form of retinitis, characterized by the presence of metalloproteinase and its species, with an effective dosage of a tetracyline analog, its salts, conjugates or derivatives sufficient to provide a anti-microbal level of concentration of the analog, its salts, conjugates or derivatives, alone or in combination with at least one other therapeutic substance, sufficient to inhibit the formation of gelatinase in the vitreous of the eyes of the patient.

It is a further object of the instant invention to provide a new and improved method of treating a patient with at least one form of retinitis, characterized by the presence of metalloproteinase and its species, which has all of the advantages of the prior art and none of its disadvantages It is another object of the instant invention to provide a new and improved method by which a patient with at least one form of retinitis, characterized by the presence of metalloproteinase and its species, may be easily and efficiently relieved of substantial advancement of the disease through the inhibition of gelatinase in the patient's vitreous.

It is another object of the instant invention to provide a new and improved method of treating at least one form of retinitis, characterized by the presence of metalloproteinase and its species, by the use of well known analogs, their salts, conjugates or derivatives of tetracycline, alone or in combination with at least one other therapeutic substance, which have hitherto been put to other uses by the prior art.

Other objects, features, and advantages of the instant invention, in its details as seen from the above, and from the following description of the preferred embodiment when considered in light of the appended claims.

DETAILED DESCRIPTION OF THE INVENTION

In its preferred embodiment, the instant invention provides a method of inhibiting metalloproteinase and at least its species of elastase, collagenase and gelatinase, occurring in at least one eye of a patient who has become inflicted with at least one eye disease, characterized by the presence of metalloproteinase. More particularly, the invention is applicable to any form of retinitis that is characterized by the presence of metalloproteinase. The particular species of retinitis contemplated by the invention includes, but is not necessarily limited to: actinic retinitis, apoplectic retinitis, central angiospastic retinitis, centralis serosa, central serious retinopathy, Coat's retinitis, exudative retinopathy; diabetic retinitis, retinitis disciformans, exudate retinitis, retinitis gravitdarum, hemorrhagica retinitis, hypertensive retinitis, Jacobson's retinitis, Jensen's retinitis, leukemic retinitis; retinitis nephritica, renal retinitis, retinitis pigmentosa, retinitis proliferans, proliferating retinitis, retinitis puntata albescens, retinitis punctate retinitis, punctate retinitis, renal retinitis, nepritica, serous retinitis, solar retinitis, splenic retinitis, leukemic retinitis, retinitis stellata, suppurative retinitis, syplilitic retinitis, retinitis syphilitica, remic retinitis, retinal microvasculopathy, cytomegalovirus retinitis, Herpes simplex retinitis, acute retinal necrosis, Herpes zoster retinitis and Toxoplasma retinochoroiditis. The instant invention also contemplates administering to the patient, an effective dosage of an analog, its salts, conjugates or derivatives of an antibacterial or a non-antibacterial tetracycline selected from the group consisting of: dedimethylaminotetracycline, 4-dedimethylamino-5-oxytetracycline, 4-dedimethylamino-7-chlorotetracycline, 5a,6-anhydro-4-hydroxy-4-dedimethylaminotetracycline, 6-demethyl-6-deoxy-4-dedimethylaminotetracycline, 6α-deoxy-5-hydroxy-4-dedimethylaminotetracycline, 4-dedimethylamino-12a-deoxytetracycline 4-dedimethylamino-11-hydroxy-12a-deoxytetracycline, minocycline, doxycycline, 7-chlorotetracycline, 5-hydroxytetracycline, 6-demethyl-7-chlorotetracycline, 6-demethyl-6-deoxy-5-bydroxy-6-methylenetetracycline, dedimethylaminotetracycline, 6-alpha-benzylthiomethylenetetracycline, mono-N-alkylated amide of tetracycline, 6fluorodemethyltetracycline, 11-alpha-chlorotetracycline, 2-acetyl-8-hydroxyl-1-tetracycline, 6-demethyl-6-deoxytetracycline, 4-de(dimethylamino)-tetracycline, 4-de(dimethylamino)-5-oxytetracycline, 4-de(dimethylamino)-7-chlortetracycline, 4-hydroxy-4-dedimethylaminotetracycline, 6-α-deoxy-5-hydroxy4-dedimethylaminotetracycline, 6α-benzylthiomethylenetetracycline, 6-fluoro-6-demethyltetracycline, 11αa-chlortetracycline, tetracyclinonitrile, tetracycline hydrochloride, ninocycline, oxytetracycline, chlortetracycline, demeclotetracycline, 4-de(dimethylamino-5-oxytetracycline, 4-de(dimethylamino)-7-chlorotetracycline, 6-α-deoxy-5-hydroxy-4-dedimethylamino-tetracycline, 11α-chlorotetracycline, demeclocycline, 7-chloro-tetracycline, 4-de(dimethylamino) tetracycline, 4-de(dimethylamino)-7 chlorotetracycline, 6-α-deoxy-5-hydroxy-4-dedimethylamino-tetracycline, 7-chloro-6-demethyl-4-dedimethylamino-tetracycline, and 4 hydroxy-4 dedimethylaminotetracycline, demeclocycline, 4-de(dimethylamino)-7-chlorotetracycline, 4-dedimethylaminotetracycline, 4-dedimethylamino-7 chlorotetracycline, 12a-deoxy-4-deoxy-4-dedimethylaminotetracycline, 12a, 4a-anhydro-4-dedimethylaminotetracycline, 7-dimethylamino-6-demethyl-6-deoxy-4dedimethylaminotetracycline, 6a-benzylthiomethylenetetracycline, 11a-chlorotetracycline, tetracycline pyrazole, 6α-deoxy-5-hydroxy4dedimethylaminodoxycycline and 12a-deoxytetracycline, 6-alpha benzylthiomethylene tetracycline, a mono-N-alkyl amide of tetracycline, a 6-fluorodemethyl tetracycline, 11-alpha-chlortetracycline, 6-demethyl-6-deoxy5-hydroxy-6-methylenetetracycline, 2-acetyl-8-hydroxy-1-tetracycline, oxytetracycline, methacycine, chlorotetracycline, 6-alpha-benzylthiomethylene tetracycline and mono-N-alkylamide tetracycline; their salts, conjugates or derivatives, and combinations thereof.

The analog, its salts, conjugates or derivatives of the instant invention may preferably be administered orally, or systemically, or by way of an injection or intravenously. Although, it may also be administered topically in the form of an ointment, drops, or other suitable topical delivery system, topical application is the least preferable.

In an alternate preferred embodiment of the invention, the above indicted tetracycline, or its salts, conjugates and/or derivatives is provided in combination with at least one other therapeutic substance. This substance may include but is not necessarily limited to at least one of the following: metronidazole, NSAID, flurbiprofen: FBP, aspirin, ibuprofen, naproxen, fenoprofen, indomethacin, phenylbutazone, berberine, cotrimoxazole, bleomycin, nicotinamide, Fluoroquinolone, ofloxacin (ROM), Rifampin, trimethoprim, sulfamethoxazole, Cyclophosphamide, Doxorubicin, Prednisone, Procarbazine, Vincristine, Quinine, ranitidine bismuth citrate, clarithromycin, Bismuth, aminoglycosides, fluoroquinolones, macrolides, Chloroquine, Falciparum, Augmentin, amoxicillin, gentamicin, rifampicin, rifampicin, rifampicin, streptomycin, artesunate, 5-fluorouracil, cisplatin, Omeprazole, Penicillins, Clarithromycin, anitidine, antibiotic ciprofloxacin quinolone (siflox), Chloroguanide, Pyrimethamine, halofantrine, amoxycillin, tobramycin, ciprofloxacin, dicloxacillin, Aminog Erytromycin lycoside, Clindamycin, Sucralfate, Triamcinolone Acetonide, Benzydamine, Isotretinoin, Ceftriaxone, Cephalosporins, Carmustine, Isoflavones, subsalicylate, lansoprazole, Estradiol, Vancomycin, ticarcillin, atovaquone, proguanil, lincomycin, spectinomycin, Somatropin, Chlorhexidine, artemisinin, azithromycin, chloramphenicol, Famotidine, mefloquine, Niacinamide, prednisolone, azathioprine, Potassium Clavulanate, tinidazole, sulfadoxine, D-penicllamine, Penicillamine, quinolines analogues, artemisinin analogues, biguanides, trimethoprim/sulfamethoxazole combination, cefuroxime, cefprozil, penicillin/lincosamides combination, penicillin/lincosamides/erythromycin combination, penicillin/tetracycline/lincosamides/erythromycin combination, Betamethasone, Colistin, Dexamethasone, Ethylmaleimide, Cysteine, Aspartic Acid, Arginine, Sodium Tetradecyl Sulfate, Trifluoroacetic Acid, Clofazimine, cefotaxime, rifamycins, trimethoprim/sulfamethoxazole combination, Polymyxin B, Nitrofurantoin, Trimethoprim/Sulfamethoxazole combination, Imipenem, Cilastatin, Methylprednisolone, imipenem/cilastatin combination, Amiloride, cefoxitin, penicillin G, ranitidine bismuth citrate (RBC)/clarithromycin combination, clarithromycin/amoxicillin combination, sulglicotide, metronidazole/lansoprazole combination, Nitrofurantoin, bismuth subsalicylate/metronidazole combination, Indoles, Polyspectran (neomycin/polymyxin B/bacitracin/gramicidin combination), Terramycin (oxytetracycline/polymyxin B combination), Pentagastrin, Pepsinogen, cefuroxime axetil, beta-lactams, quinolones, trimethoprim/sulfamethoxazole combination, clarithromycin/metronidazole combination, clarithromycin/amoxycillin combination, amoxycillin/metronidazole combination, isopropyl-beta-D-thiogalactopyranoside (IPTG), Isopropyl Thiogalactoside, tenidap, Oxacillin, Trimethoprim/Sulfamethoxazole combination, ampicillin, lincomycin/spectinomycin combination, or Interleukin6.

Dosages of the analog, its salts, conjugates and/or derivatives, alone or in combination with the at least one other therapeutic substance, may range in amounts of from about 0.1 mg/kg/day to about 50 mg/kg/day; more preferably in amounts of from about 10.0 mg/kg/day to about 30 mg/kg/day; and most preferably amounts of about 20.0 mg/kg/day to about 25.0 mg/kg/day. Dosages of the at least one other therapeutic substance, when administered in combination with the analog, it salts, conjugates and/or derivatives, may also range in amounts of from about 0.1 mg/kg/day to about 50 mg/kg/day; more preferably in amounts of from about 10.0 mg/kg/day to about 30 mg/kg/day; and most preferably amounts of about 20.0 mg/kg/day to about 25.0 mg/kg/day.

The dosage of tetracycline analog, alone or in combination, may be administered orally or systemically. When applied topically the dosage may be in the form of an ointment, drops, or other suitable topical delivery system. When applied systemically, the dosage may be administered by way of injection, intravenously or orally.

Although the invention most preferably contemplates treatment of the vitreous of the eye of a patient inflicted with at least one form of retinitis, characterized by the presence of metalloproteinase and its species, it is equally applicable to the treatment of any disease which causes the formation of metalloproteinase and any of its species, elastase, gelatinase, and collagenase, within any part of the eye of a patient, including but not limited to: the sclera, iris, choroid, retina, vitreous and cornea.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

Having described a preferred embodiment of my invention, what I claim and desire to secure by U.S. Letters Patent is:

1. A method for treating retinitis in an eye of a patient wherein said retinitis is characterized by the presence of metaloproteinase comprising:

administering to said patient an antibacterial or non-antibacterial analog of tetracycline, its salts, conjugates, or derivatives or combinations thereof in a dosage amount effective to prohibit the further formation of said metaloproteinase, said metaloproteinase being a member selected from the group consisting of collagenase, elastase and gelatinase and combinations thereof.

2. The method of claim 1 wherein said retinitis is a disease of the eye selected from the group consisting of actinic retinitis, apoplectic retinitis, central angioplastic retinitis, centralis serious retinopathy, Coat's retinitis, exudative retinopathy, diabetic retinitis, retinitis disciformans, exudate retinitis, retinitis gravitdarum, hemorrthagica retinitis, hypertensive retinitis, Jacobson's retinitis, leukemic retinitis, retinitis nephritica, renal retinitis, retinitis pigmentosa, retinitis proliferans, proliferating retinitis, retinitis putata albescerns, punctate retinitis, renal retinitis, nepritica, serous retinitis, solar retinitis, splenic retinitis, retinitis stellata, supporative retinitis, syplititic retinitis, retinitis syphlitica, remic retinitis, retinal microvasculopathy, cytomegalovirus retinitis, Herpes simplex retinitis, acute retinal necrosis, Herpes zoster retinitis and Toxoplasma retinochoroditis.

3. The method of claim 1 wherein said tetracycline analog is an antibacterial tetracycline, a non-antibacterial tetracycline or combinations thereof and is a member selected from the group consisting of dedimethylaminotetracycline, 4-dedimethylamino5-oxytetracycline, 4-dedimethylamino-7-chlorotetracycline, 5-alpha-6-anhydro-4-hydroxy-4-dedimethylaminotetracycline, 6-demethyl-6-deoxy-4-dedimethylaminotetracycline, 6-alpha-deoxy-5-hydroxy-4-dedimethylaminotetracycline, 4-dedimethylamino-12-alpha-deoxytetracycline, 4-dedimethylamino-11-hydroxy-12-alpha-deoxytetracycline, minocycline, doxycycline, 7-chlorotetracycline, 5-hydroxytetracycline, 6-demethyl-7-chlorotetracycline, 6-demethyl-6-deoxy-5-hydroxy-6-methylenetetracycline, 6-alpha-benzylthiomethylenetetracycline, mono-N-alkylated amide of tetracycline, 6-fluorodemethyltetracyclune, 11-alpha-chlorotetracycline, tetracyclinonitrile, tetracycline hydrochloride, oxyteracycline, chlorotetracycline, 7-chloro-6-demethyl-4-dedimethylaminotetracycline, 2-alpha-deoxy-4-deoxy-4-dedimethylaminotetracycline, 12-alpha-4-alpha-anhydro-4-dedimethylaminotetracycline, 7-dimthylamino-6-demeyhl-6deoxy-4-dedimethylaminotetracycline, tetracycline pyrazole, 6alpha-deoxy-5-hydroxy-4-dedimethylaminotetracycline, 12-alpha-deoxytetracycline, methyacycline, their salts, conjugates or derivatives and combinations thereof.

4. The method of claim 1 wherein said tetracycline analog is administered in a dosage amount of from about 0.1 to about 100 mg/kg/day.

5. The method of claim 4 wherein said dosage amount is from about 10 to about 50 mg/kg/day.

6. The method of claim 4 wherein said dosage amount is from about 20 to about 25 mg/kg/day.

7. The method of claim 1 wherein said tetracycline analog is administered orally, systemically, topically, intravenously or by injection.

* * * * *